United States Patent [19]

Child

[11] 4,301,796

[45] Nov. 24, 1981

[54] METHOD AND APPARATUS FOR DISPENSING FLUID

[75] Inventor: Francis W. Child, Eagle Bend, Minn.

[73] Assignee: Child Laboratories Inc., Eagle Bend, Minn.

[21] Appl. No.: 60,916

[22] Filed: Jul. 26, 1979

[51] Int. Cl.³ ........................ A61M 1/00; A61M 3/00

[52] U.S. Cl. ................................ 128/213 R; 128/232; 128/242; 128/261; 119/14.19; 206/438

[58] Field of Search ............... 128/213 R, 214 D, 222, 128/223, 224, 232, 242, 243-244, 260-261, 341, 348-351, 231, 240, 248, 251; 119/14.19, 14.20, 14.21; 206/438

[56] References Cited

U.S. PATENT DOCUMENTS

| | | | |
|---|---|---|---|
| 2,856,932 | 10/1958 | Griffitts | 128/294 |
| 2,902,146 | 9/1959 | Doherty | 206/63.2 |
| 3,053,385 | 9/1962 | Spees | 206/63.2 |
| 3,175,553 | 3/1965 | Mattson | 128/2 |
| 3,186,628 | 6/1965 | Rohde | 229/66 |
| 3,282,412 | 11/1966 | Corella et al. | 206/47 |
| 3,419,134 | 12/1968 | Fitts | 206/47 |
| 3,421,509 | 1/1969 | Fiore | 128/343 X |
| 3,539,794 | 11/1970 | Rauhut et al. | 240/2.25 |
| 3,570,612 | 3/1971 | Polyak | 128/261 X |
| 3,604,616 | 9/1971 | Greif | 229/55 |
| 3,703,898 | 11/1972 | Zackheim | 128/261 |
| 3,862,684 | 1/1975 | Schmitt | 200/277 |
| 3,917,116 | 2/1974 | Mason | 222/92 |
| 4,011,947 | 3/1977 | Sawyer | 206/363 |
| 4,027,670 | 6/1977 | Bronner | 128/261 |
| 4,062,363 | 12/1971 | Bonner, Jr. | 128/349 R |
| 4,168,000 | 9/1979 | MacRitchie | 206/63.3 |

*Primary Examiner*—Stephen C. Pellegrino
*Attorney, Agent, or Firm*—Burd, Bartz & Gutenkauf

[57] ABSTRACT

A dilator for use in a bovine animal's teat for controlling the flow of fluid from the teat is packaged in an envelope containing a disinfectant solution. A collapsible dispensing bag containing material, as antibiotics, is located within the envelope. An elongated dispensing tube connected to the bag carries the material from the bag to the teat duct accommodating the dilator. The envelope has releasable seals which permit the envelope to be opened to expose the dilator. The envelope is used as a cover to maintain the dilator in a sterile condition as it is inserted into the duct of the teat. The material in the bag is moved from the bag by applying a squeezing force to the envelope and bag. After all of the material is squeezed from the bag, the dispenser and envelope are removed from the teat and dilator.

48 Claims, 9 Drawing Figures

METHOD AND APPARATUS FOR DISPENSING FLUID

SUMMARY OF INVENTION

The invention is directed to a method and apparatus for dispensing material, such as a drug material, into a body duct, passage, or cavity. The apparatus has first means adapted to be located in the body passage. The first means has a member carrying a normally closed one-way valve operable to restrict flow of fluids and materials out of the body passage. The first means is located in a chamber of an envelope. A second dispensing means is also located in the chamber of the envelope. The second means has a flexible bag storing the material to be dispensed into the body passage and a tube connected to the bag for carrying material from the bag to the body passage when the first means is located in the body passage.

The apparatus is a dilator used with the teat of a mammal, such as a bovine animal or a caprine animal, for controlling the flow of fluid from the teat and restricting the movement of external foreign material into the teat duct and udder of the animal. The dilator has a body carrying a plurality of angularly disposed fingers. The forward ends of the fingers are joined to a cylindrical member or sleeve having a longitudinal passage. A one-way valve is joined to the body to control the flow of fluid out of the dilator. The valve has flexible side walls terminating in lips surrounding a normally closed mouth. A dispensing means has a flexible bag and an elongated tube that extends through the mouth for delivering the drug materials to the teat duct and udder through the dilator adjacent the forward end of the sleeve.

The dilator is packaged in an envelope containing a dispensing means. The envelope is a two-sheet member that can be opened to expose the dilator. The envelope serves to shield the dilator during the insertion of the dilator into the milk duct and contains a disinfectant which disinfects the outside of the teat. After the dilator has been inserted into the teat duct, the bag is squeezed to force the material in the bag through the tube into the teat duct and cistern of the udder. The envelope functions as a storage means for the insertable dilator and a support for the dispensing unit. The envelope also functions as a shipping and storage container which maintains the dilator in a sterile condition.

The method comprises the opening of the envelope to expose the dilator. The exposed dilator is inserted in the milk duct from the discharge end thereof. The envelope serves as a cover or shield protecting the dilator from external contamination during the insertion procedure. The material in the bag is dispensed by compressing the bag to force the material through the tube and into the body passage or milk duct. After the material has been dispensed, the envelope, bag, and tube are removed from the teat and dilator. The dilator remains in the milk duct of the teat.

IN THE DRAWINGS

Figure 9:
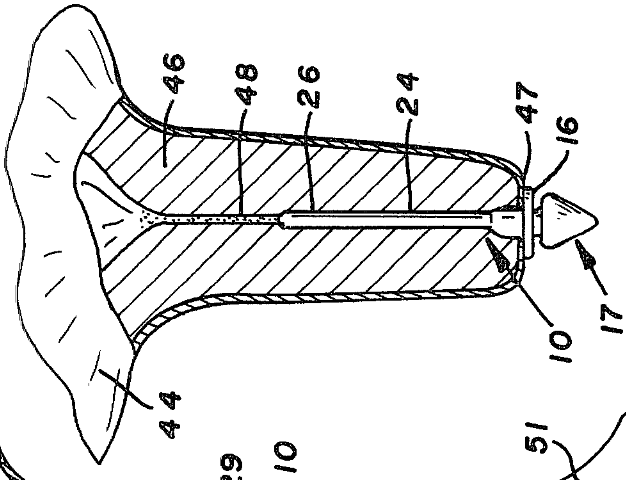
Figure 8:
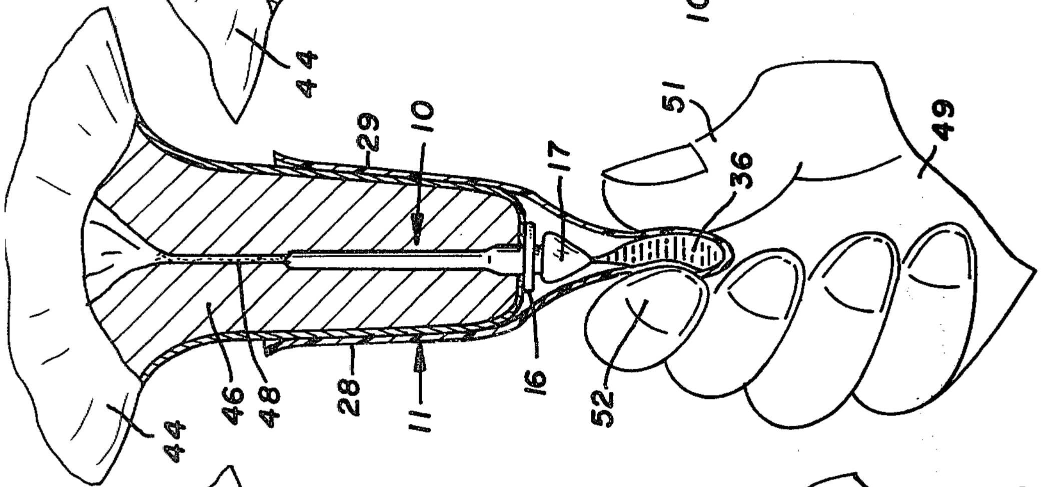
Figure 7:
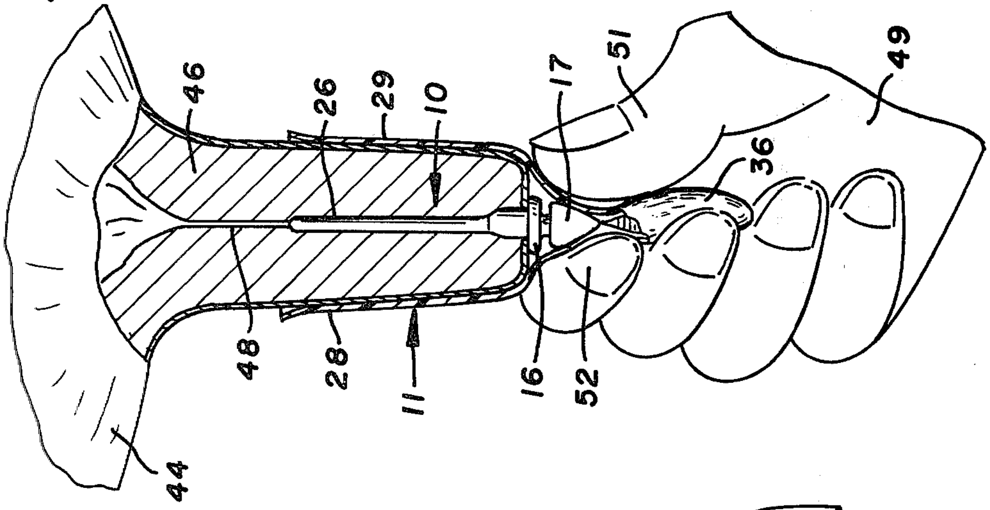
Figure 6:
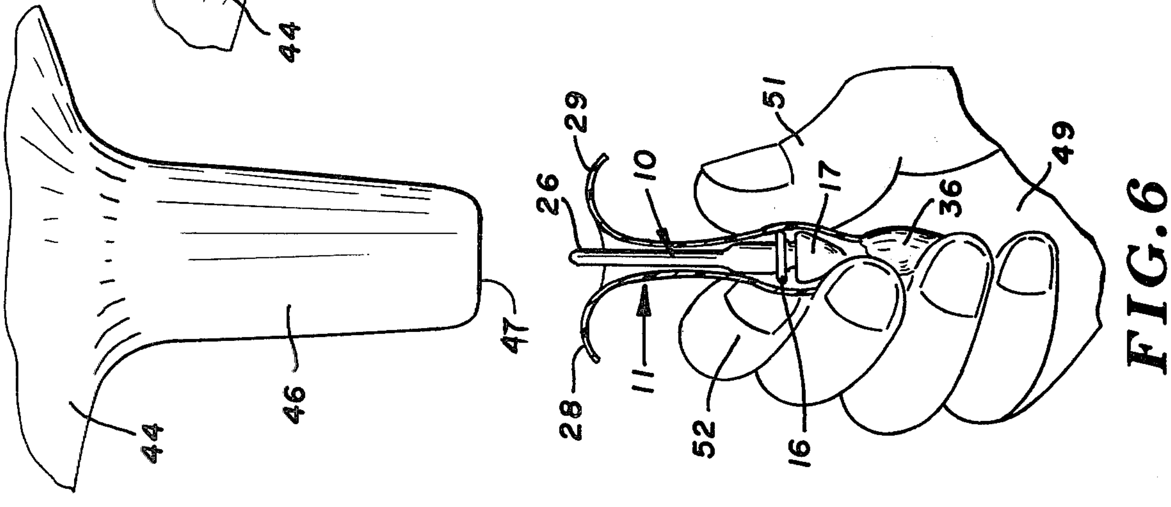

FIGS. 6, 7, and 8 illustrate the method of inserting the dilator into a milk duct of a teat; and FIG. 9 is an elevational view of the dilator located in the teat shown in section.

DETAILED DESCRIPTION OF PREFERRED EMBODIMENT

Figure 1:
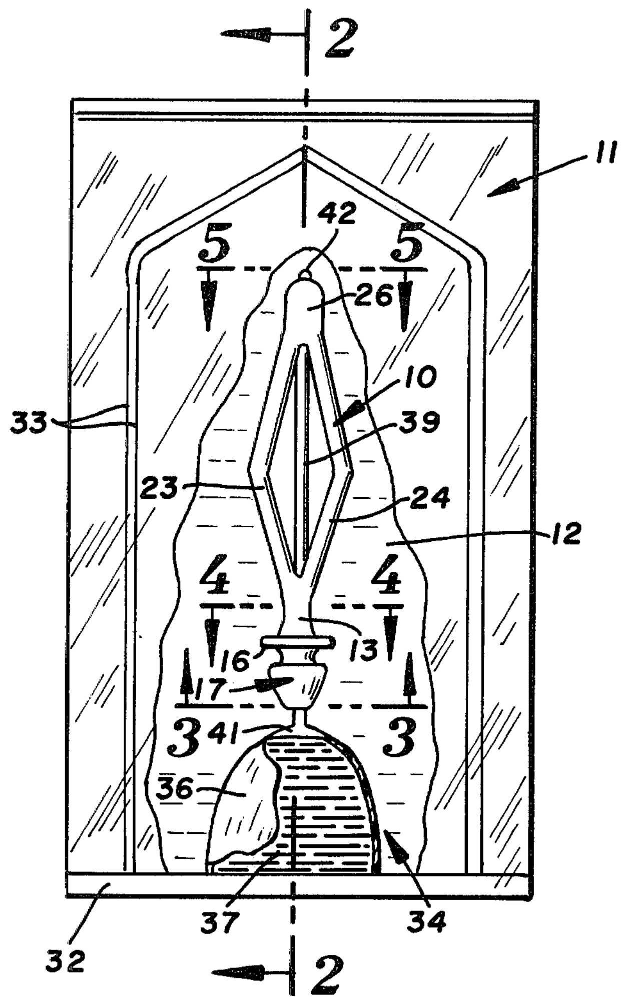
FIG. 1 is a front elevational view of a teat dilator located in an applicator envelope with parts of the envelope broken away to illustrate the dilator.
Figure 2:
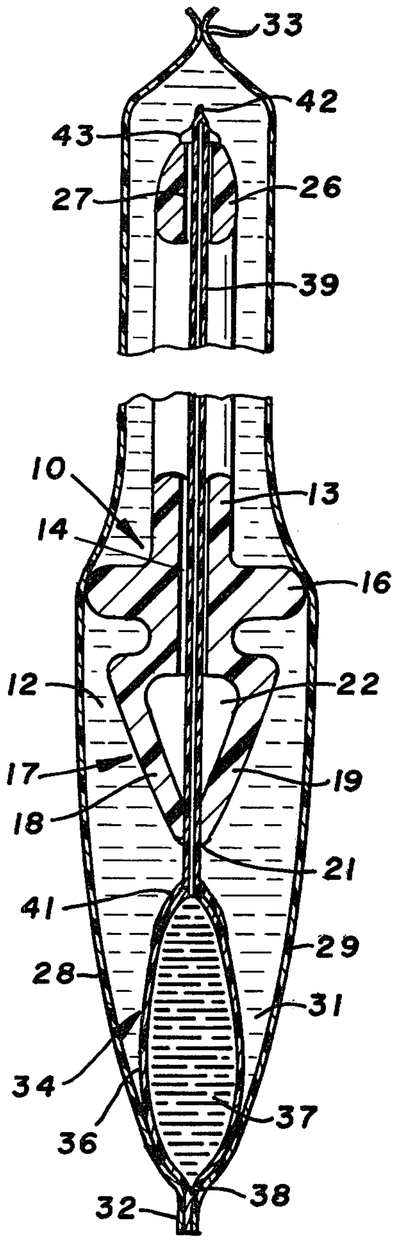
FIG. 2 is an enlarged foreshortened sectional view taken along the line 2—2 of FIG. 1.
Figure 3:
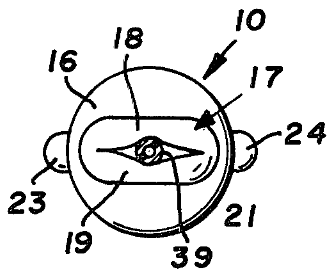
FIG. 3 is an enlarged sectional view taken along the line 3—3 of FIG. 1.
Figure 4:
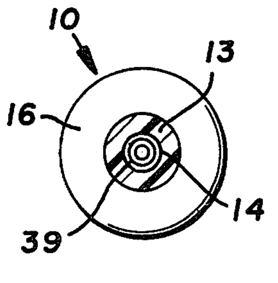
FIG. 4 is an enlarged sectional view taken along the line 4—4 of FIG. 1.
Figure 5:
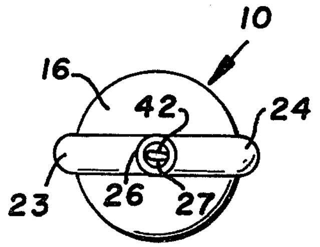
FIG. 5 is an enlarged top plan view taken along the line 5—5 of FIG. 1.

Referring to FIGS. 1 and 2, there is shown a dilator indicated generally at 10 for controlling the flow of a fluid in a duct or canal, such as a milk duct in a cow's teat. Dilator 10 is an apparatus that can be inserted or implanted in a duct, passage, or cavity of living tissue to control the flow of fluid from the tissue. Dilator 10 is located within an application envelope indicated generally at 11. Envelope 11 has a chamber 12 accommodating the dilator. Envelope 11 is a sealed package adapted to maintain the dilator in a sterile condition that is used to insert the dilator into the milk duct of a teat and to dispense material into the milk duct. Dilator 10 is hereinafter described as an apparatus used in a milk duct of a milk cow's teat. Dilator 10 can be any apparatus used in a duct, passage, or cavity of a body, including a living body, to provide for and control the flow of fluid and materials in the body.

Dilator 10 has a cylindrical body 13 having a longitudinal passage 14. The mid-section of body 13 has an outwardly directed annular rib or flange 16 which serves as a stop indicating the inserted position of the dilator in the teat duct of an animal.

A one-way valve 17 is integral with the lower portion of body 13. Valve 17 has downwardly converging side walls 18 and 19 which terminate in lips that form a normally closed mouth 21. Mouth 21 is formed by an elongated opening or slit which can be opened to provide access to a chamber 22 located between flexible side walls 18 and 19. Chamber 22 is open to the bottom of passage 14.

A pair of flexible fingers 23 and 24 extend upwardly from and are integral with body 13. Each finger has an outwardly directed angular configuration comprised of two linear segments angularly related to each other at an angle of about 120 degrees. The upper or outer end of fingers 23 and 24 are joined to a cylindrical sleeve or head 26. Head 26 has a spherical forward end to facilitate the insertion of the head into the duct of the cow's teat. Head 26 has a longitudinal passage 27 that is aligned with the passage 14 and body 13.

Dilator 10 can have other shapes and finger structures. Examples of other dilators are disclosed in my co-pending U.S. patent application Ser. No. 055,994, filed July 9, 1979. The dilator structures of this Application are incorporated herein by reference.

Envelope 11 comprises a pair of side-by-side sheet members 28 and 29 which form the cavity or chamber 12 accommodating dilator 10. Sheet members 28 and 29 are flat and flexible plastic films. The chamber 12 can contain a medicinal or disinfectant solution, such as an iodine solution for use to disinfect the outer skin of the cow's teat during the insertion of the dilator into the milk duct of the teat. Sheet members 28 and 29 have a generally rectangular shape with a transverse closed bottom or end 32 and a releasable side and top seals 33.

Bottom 32 is a transverse heat seal seam that is closed after dilator 10, fluid dispenser 34, and disinfectant solution is placed in the envelope chamber. Seals 33 are continuous beads of pressure sensitive adhesive that hermetically seal sheet members 28 and 29 to completely enclose chamber 12.

A fluid dispenser indicated generally at 34 is located in chamber 12 adjacent the bottom closed end 32. Fluid dispenser 34 comprises a flexible bag 36 having flexible side walls closing a chamber 37 containing a fluid. The fluid can be an antibiotic, such as penicillin or streptomycin. Other types of fluids and semi-fluids can be stored in bag 36. The fluid can be a liquid or flowable solid, as a drug or dye that is to be dispensed into the fluid canal in the tissue. The fluid and solids are used herein as a material that is dispensed in the milk duct and udder.

Bag 36 has an end 38 sealed with end 32. An elongated tube 39 is joined to the upper end of bag 36 with a connector or seal unit 41. Tube 39 extends through mouth 21, chamber 22, and passages 14 and 27. The upper or outer end of tube 39 and end 42 is closed and has an enlarged tip or bulb 43 that bears against the top of head 26. Bulb 43 retains the tube 39 in the passage 27 during the insertion of the dilator into the canal. End 42 can be heat sealed together or contain a plug that flows from the end 42 on the application of pressure to bag 36. End 42 can be open when a semi-fluid and flowable solids are located in bag 36. Tube 39 is a flexible plastic tubular member. Metal and rigid plastic tubes can be used in lieu of plastic tube 39.

Referring to FIG. 9, there is shown an udder 44 of a bovine animal, such as a milk cow. A teat 46 projects downwardly from udder 44. Teat 46 has a lower end 47 providing an opening for a milk duct 48 which extends from the teat end 47 up into the base of udder 44. A sphincter muscle closes the discharge or exit end of milk duct 48. Dilator 10 is located in the lower portion of milk duct 48 and provides a passage for the flow of milk and fluids from the upper part of the milk duct through the valve 17 to a receptacle.

The method of treating teat 46 with the use of dilator 10 is shown in FIGS. 6–8. The udder and teat 46 are first washed to clean the outside of the teat. Referring to FIG. 6, envelope 11 is initially opened by separating the upper end of the sheet members 28 and 29. This exposes dilator head 26. Teat 46, previously cleaned by washing, is held in the vertical position so that dilator end 26 can be aligned with discharge end of milk duct 48. Dilator 10 is held with the hand 49 between the thumb 51 and first finger 52. Bag 36 is located in the palm of the hand and not subjected to compressive force. The outside of the teat 46 is washed or covered with the treatment solution in chamber 12 as the envelope 11 is slipped over teat 46, as shown in FIG. 7. Thumb 51 and first finger 52 grip the valve 17 to locate the flange 16 in engagement with the bottom of teat 46. The sheet members 48 and 49 move up along the outside of teat 46 to locate the lower end of the teat 46 in the chamber 12 of envelope 11.

Referring to FIG. 8, dilator 10 is located in the inserted position in milk duct 48. Material 37 in bag 36 is dispensed into milk duct 48 and lower portion of the udder 44 by applying a squeezing or compressive force to bag 36. This is done with the thumb 51 and first finger 52 of the hand 49. The material in bag 36 is forced up through the tube 39 and discharged into milk duct 48. The closed end 42 on the tube 39 is opened in response to the pressure on bag 36. The continued pressure on or squeezing of the bag 36 will force material 37 up the milk duct 48 into the lower cavity or cistern in the lower portion of udder 44. When bag 36 is collapsed, the envelope 11 and bag 36, along with tube 39, is removed from the teat and dilator 10. The valve 17 closes, since the side walls 18 and 19 are flexible and bias mouth 21 to its normally closed position to prevent the entrance of foreign materials into milk duct 48 and prevent the fluid and material from flowing out of the teat canal and lower portion of the udder. Valve 17 also prevents the flow of milk and fluids from the milk duct 48 under normal or natural pressures in the teat and udder. The valve 17 will open when the teat is subjected to a milking pressure as a result of either hand or machine milking.

While there has been shown and described the preferred apparatus and method for treating a living tissue having a fluid duct, as a cow's teat, it is understood that changes in the dilator structure, envelope structure, and the antiseptic and medicinal solutions used in the envelope and bag may be made by those skilled in the art without departing from the invention. The invention is defined in the following claims.

The embodiments of the invention in which an exclusive property or privilege is claimed are defined as follows:

1. An apparatus for dispensing material into the milk duct of a cow's teat comprising: a dilator having means insertable into the milk duct and a one-way valve to restrict movement of material into the milk duct, an envelope having a chamber accommodating the dilator, and dispensing means located in said chamber, said dispensing means having a flexible bag accommodating the material to be dispensed into the milk duct, and means to carry the material from the bag through the one-way valve and into the milk duct when the dilator is inserted into the milk duct.

2. The apparatus of claim 1 wherein: said means of the dilator has means having a passage, said means to carry the material comprising tubular means extended through said passage.

3. The apparatus of claim 2 including: means on said tubular means to releasably hold the tubular means on the means having a passage.

4. The apparatus of claim 1 wherein: said envelope comprises two sheet members having adjacent portions, releasable means attaching the adjacent portions of the sheet members to enclose the chamber, said sheet members being separable to expose the dilator.

5. The apparatus of claim 1 including: means attaching the bag to the sheet members.

6. The apparatus of claim 5 wherein: the means attaching the bag to the sheet members comprises a seal joining adjacent edge portions of the sheet members to a portion of the bag.

7. The apparatus of claim 1 wherein: said dilator has a body with a longitudinal passage, said means insertable into the milk duct being attached to the body, said one-way valve having flexible walls attached to the body, said walls having lips normally closing a mouth, said means to carry the fluid from the bag extending through said mouth and passage in the body.

8. The apparatus of claim 7 wherein: said means insertable into the milk duct include a plurality of flexible fingers, said fingers having forward ends, sleeve means secured to the forward ends of the fingers, said sleeve means having a passage aligned with the passage in the body, said means to carry fluid from the bag comprising an elongated tubular member extended through the mouth of the one-way valve means, the passage in the body, and the passage in the sleeve means, said tubular member having a discharge end located forwardly of said sleeve means.

9. The apparatus of claim 8 including: means on the tubular member engageable with the sleeve means to releasably hold the tubular member on the sleeve means.

10. An apparatus for dispensing material into a passage of a body comprising: first means adapted to be located in the passage, said first means having a tubular body having a passage and a one-way valve operable to restrict movement of material into said passage of the body, an envelope having a chamber accommodating the first means, and second means located in said chamber of the envelope operable to dispense material into the passage of the body, said second means having a bag accommodating material to be dispensed, and tubular means to carry the material from the bag through the one-way valve and passage in the tubular body to the passage of the body when the first means is located in the passage of the body.

11. The apparatus of claim 10 wherein: said one-way valve includes a plurality of flexible side walls, said side walls terminating in lips surrounding a normally closed mouth.

12. An apparatus for dispensing material into a passage of a body comprising: first means adapted to be located in the passage, said first means having a one-way valve operable to restrict the movement of material into said passage, said one-way valve includes a pair of flexible side walls, said side walls terminating in lips surrounding a normally closed mouth, an envelope having a chamber accommodating the first means, and second means located in said chamber of the envelope operable to dispense material into the passage, said second means having material to be dispensed into said passage and carrying the material to the passage when the first means is located in the passage.

13. The apparatus of claim 12 wherein: the first means includes means having a passage, said second means including tubular means to carry material, said tubular means extending through the passage in the means having a passage.

14. The apparatus of claim 13 including: means on said tubular means to releasably hold the tubular means on the sleeve.

15. The apparatus of claim 12 wherein: said first means has a body with a longitudinal opening, said one-way valve being attached to said body, and means attached to the body adapted to be inserted into the passage of the body.

16. The apparatus of claim 15 wherein: said means attached to the body includes a plurality of flexible fingers having forward ends and a head secured to the forward ends of the fingers.

17. The apparatus of claim 12 including: means attaching the second means to the envelope.

18. An apparatus for dispensing material into a passage of a body comprising: first means adapted to be located in the passage, said first means having a one-way valve operable to restrict movement of material into said passage, an envelope having a chamber accommodating the first means, and second means located in said chamber of the envelope operable to dispense material into the passage, said second means includes a bag accommodating the material to be dispensed and means to carry the material from the bag to the passage when the first means is located in the passage.

19. The apparatus of claim 18 wherein: said envelope comprises two side-by-side sheet members having adjacent side portions and end portions, releasable means attaching adjacent side portions and one end portion of the sheet members to close the chamber, and means closing the other end of the sheet members, said releasable means allowing the sheet members to be separable to expose the first means.

20. The apparatus of claim 19 wherein: said means closing the other end of the sheet members attaching the bag to the sheet members.

21. The apparatus of claim 18 wherein: the means to carry material from the bag extends through the one-way valve.

22. The apparatus of claim 21 wherein: the means to carry material from the bag is a tubular member extended through the one-way valve.

23. The apparatus of claim 22 wherein: the first means has means having a longitudinal passage, said tubular member extended through said passage.

24. An apparatus for dispensing material into a passage of a body comprising: first means adapted to be located in the passage, an envelope having a chamber accommodating the first means, and second means located in the chamber of the envelope operable to dispense material into the passage, said second means including bag means accommodating material to be dispensed and means to carry the material from the bag means to the passage when the first means is located in the passage.

25. The apparatus of claim 24 wherein: the first means includes a tubular body having a passage, said means to carry the material from the bag means comprises tubular means to carry the material from the bag means through the passage in the tubular body.

26. The apparatus of claim 24 wherein: the first means includes means having a passage, said means to carry the material from the bag means includes tubular means to carry material, said tubular means extending through the passage in the means having a passage.

27. The apparatus of claim 26 including: means on said tubular means to releasably hold the tubular means on the sleeve.

28. The apparatus of claim 24 wherein: said first means has a body with a longitudinal opening, finger means attached to the body, said finger means adapted to be inserted into the opening of the body.

29. The apparatus of claim 28 wherein: said finger means includes a plurality of flexible fingers having forward ends and a head secured to the forward ends of the fingers.

30. The apparatus of claim 24 wherein: said envelope includes means to attach the bag means to the envelope.

31. The apparatus of claim 24 wherein: said envelope comprises two side-by-side sheet members having adjacent side portions and end portions, releasable means attaching adjacent side portions and one end portion of the sheet members to close the chamber, and means closing the other end of the sheet members, said releasable means allowing the sheet members to be separable to expose the first means.

32. The apparatus of claim 31 wherein: said means closing the other end of the sheet members attaching the bag means to the sheet members.

33. The apparatus of claim 24 wherein: means to carry the material from the bag means includes a tubular member to carry the material to be dispensed.

34. The apparatus of claim 33 including: means securing the bag means to the envelope.

35. A method of dispensing material into the milk duct of a teat of an amimal with a dilator located within an envelope, a flexible bag located within the envelope, and tubular means connected to the bag for carrying material from the bag through the dilator and discharging the material into the milk duct comprising: opening the envelope to expose the dilator, inserting the dilator in the milk duct of the teat from the discharge end thereof, dispensing the material in the bag into the milk duct by compressing the bag to force the material in the bag to move through the tubular means into the milk duct, and removing the envelope, bag and tubular means from the dilator, said dilator remaining in the milk duct of the teat.

36. The method of claim 35 wherein: the envelope is partly opened to expose a forward portion of the dilator, said envelope being used as a cover during the insertion of the dilator in the milk duct of the teat and the dispensing of material from the bag.

37. The method of claim 35 wherein: said dilator has a one-way valve restricting movement of fluid out of the milk duct, said tubular means extended through said valve so that the material moves through said valve when the bag is compressed.

38. The method of claim 35 wherein: the dilator is inserted into the milk duct by using the envelope as a shield around the dilator with the insertion force being applied to the dilator through the envelope.

39. The method of claim 35 including: shielding the dilator with the envelope during the insertion of the dilator into the milk duct of the teat.

40. The method of claim 35 including: covering part of the teat with the envelope when the dilator is located in the milk duct of the teat.

41. The method of claim 35 including: shielding the bag with the envelope during the dispensing of the material from the bag.

42. A method of dispensing material into a passage of a body, said passage having a discharge end, with means adapted to be located in the passage, said means being located within an envelope, a flexible bag located within the envelope, and tubular means connected to the bag for carrying material from the bag through the means and discharging the material into the passage comprising: opening the envelope to expose the means, inserting the means in the passage from the discharge end thereof, dispensing the material in the bag into the passage by compressing the bag to force the material in the bag to move through the tubular means into the passage and removing the envelope bag and tubular means from the means, said means remaining in the passage.

43. The method of claim 42 wherein: the envelope is partly opened to expose a forward portion of the means, said envelope being used as a cover during the insertion of the means in the passage of the teat and the dispensing of material from the bag.

44. The method of claim 42 wherein: said means has a one-way valve restricting movement of fluid out of the passage, said tubular means extended through said valve so that the material moves through said valve when the bag is compressed.

45. The method of claim 42 wherein: the means is inserted into the passage by using the envelope as a shield around the means with the insertion force being applied to the means through the envelope.

46. The method of claim 42 including: shielding the means with the envelope during the insertion of the means into the passage.

47. The method of claim 42 including: covering part of the body with the envelope when the means is located in the passage.

48. The method of claim 42 including: shielding the bag with the envelope during the dispensing of the material from the bag.

* * * * *